(12) United States Patent
Nyberg et al.

(10) Patent No.: US 11,690,752 B2
(45) Date of Patent: *Jul. 4, 2023

(54) METHOD OF PROVIDING AN OSTOMY DEVICE THAT IS SHAPE-ADJUSTABLE TO CONFORM TO A BULGE OR A HERNIA ASSOCIATED WITH A STOMA

(71) Applicant: Coloplast A/S, Humlebaek (DK)

(72) Inventors: Rene Ferm Nyberg, Hilleroed (DK); Richard Morgan Hickmott, Helsingoer (DK); Marie Bay Borg, Broenshoej (DK); Martin Pråme, Svedala (SE); Claus Oellgaard, Fredensborg (DK); Niels Pinholt, Roskilde (DK)

(73) Assignee: Coloplast A/S, Humlebaek (DK)

( * ) Notice: Subject to any disclaimer, the term of this patent is extended or adjusted under 35 U.S.C. 154(b) by 162 days.

This patent is subject to a terminal disclaimer.

(21) Appl. No.: 17/331,668

(22) Filed: May 27, 2021

(65) Prior Publication Data

US 2021/0282959 A1     Sep. 16, 2021

Related U.S. Application Data

(63) Continuation of application No. 15/558,644, filed as application No. PCT/DK2016/050074 on Mar. 16, 2016, now Pat. No. 11,051,969.

(30) Foreign Application Priority Data

| Mar. 16, 2015 | (DK) | .......................... PA 2015 70150 |
| Apr. 14, 2015 | (DK) | .......................... PA 2015 70215 |
| Sep. 11, 2015 | (DK) | .......................... PA 2015 70585 |

(51) Int. Cl.
  *A61F 5/443*     (2006.01)
  *A61F 5/445*     (2006.01)
  *A61F 5/44*      (2006.01)

(52) U.S. Cl.
  CPC .............. *A61F 5/443* (2013.01); *A61F 5/445* (2013.01)

(58) Field of Classification Search
  CPC ............ A61F 5/443; A61F 5/445; A61F 5/44
  See application file for complete search history.

(56) References Cited

U.S. PATENT DOCUMENTS

| 257,063 A | 4/1882 | Phillips |
| 2,675,001 A | 4/1954 | Jones |

(Continued)

FOREIGN PATENT DOCUMENTS

| CN | 201005837 Y | 1/2008 |
| CN | 301202523 S | 5/2010 |

(Continued)

*Primary Examiner* — Guy K Townsend
(74) *Attorney, Agent, or Firm* — Coloplast Corp., Coloplast A/S; Nick Baumann

(57) ABSTRACT

We disclose a method of providing a user or a healthcare worker with an ostomy device that is shape-adjustable to conform to skin around a stoma associated with a bulge or a hernia. The ostomy device is configured to invert from a storage configuration to a use configuration by inverting a substantially convex shape of a proximal side of a base plate to a substantially concave shape and stabilizing the base plate in the use configuration by contacting the inner radial periphery of the reinforcing structure with a distal surface of the base plate.

17 Claims, 2 Drawing Sheets

(56) References Cited

U.S. PATENT DOCUMENTS

| | | | |
|---|---|---|---|
| 2,684,675 A * | 7/1954 | Murle | A61F 5/445 |
| | | | 604/341 |
| 2,928,393 A | 3/1960 | Marsan | |
| 3,074,404 A | 1/1963 | Robinson | |
| 3,557,790 A | 1/1971 | Hauser | |
| 3,964,485 A | 6/1976 | Neumeier | |
| 4,109,657 A * | 8/1978 | Carrington | A61F 5/448 |
| | | | 604/338 |
| 4,213,458 A | 7/1980 | Nolan | |
| 4,219,023 A * | 8/1980 | Galindo | A61F 5/445 |
| | | | 604/344 |
| 4,253,460 A | 3/1981 | Chen et al. | |
| 4,367,732 A * | 1/1983 | Poulsen | A61L 28/0011 |
| | | | 602/56 |
| 4,387,713 A | 6/1983 | Calanni | |
| 4,419,100 A | 12/1983 | Alexander | |
| 4,460,363 A | 7/1984 | Steer et al. | |
| 4,475,908 A * | 10/1984 | Lloyd | A61L 24/06 |
| | | | 604/339 |
| 4,477,325 A | 10/1984 | Osburn | |
| 4,534,768 A | 8/1985 | Osburn et al. | |
| 4,681,574 A | 7/1987 | Eastman | |
| 4,710,182 A | 12/1987 | Bryson | |
| 4,717,385 A * | 1/1988 | Cameron | A61M 25/02 |
| | | | 285/194 |
| 4,723,952 A | 2/1988 | Esposito | |
| 4,762,738 A * | 8/1988 | Keyes | A61F 13/47 |
| | | | 428/34.3 |
| 4,834,731 A * | 5/1989 | Nowak | A61F 5/448 |
| | | | 604/339 |
| 4,872,464 A * | 10/1989 | Loeb | A61F 6/04 |
| | | | 604/352 |
| 4,973,323 A | 11/1990 | Kaczmarek et al. | |
| 5,000,748 A * | 3/1991 | Fenton | A61F 5/443 |
| | | | 604/340 |
| 5,004,464 A * | 4/1991 | Leise, Jr. | A61F 5/448 |
| | | | 604/338 |
| 5,051,259 A * | 9/1991 | Olsen | A61F 13/0213 |
| | | | 428/355 R |
| D323,213 S | 1/1992 | Iacone | |
| 5,079,843 A | 1/1992 | Shelton et al. | |
| 5,125,917 A * | 6/1992 | Whealin | A61F 5/448 |
| | | | 604/340 |
| 5,163,930 A | 11/1992 | Blum | |
| 5,167,651 A | 12/1992 | Leise et al. | |
| 5,261,708 A | 11/1993 | Steer | |
| D345,418 S | 3/1994 | Fenton | |
| 5,312,382 A | 5/1994 | Metz | |
| 5,316,607 A | 5/1994 | Johnsen et al. | |
| 5,386,835 A * | 2/1995 | Elphick | A61F 15/004 |
| | | | 128/849 |
| 5,429,625 A * | 7/1995 | Holmberg | A61F 5/448 |
| | | | 604/338 |
| 5,501,678 A * | 3/1996 | Olsen | A61F 5/443 |
| | | | 604/344 |
| 5,503,635 A | 4/1996 | Sauer et al. | |
| 5,607,413 A * | 3/1997 | Holmberg | A61F 5/448 |
| | | | 604/338 |
| 5,618,276 A * | 4/1997 | Leise, Jr. | A61F 5/445 |
| | | | 604/338 |
| 5,636,643 A * | 6/1997 | Argenta | A61M 1/782 |
| | | | 602/42 |
| 5,683,286 A | 11/1997 | Kielland | |
| 5,714,225 A | 2/1998 | Hansen et al. | |
| 5,730,735 A | 3/1998 | Holmberg et al. | |
| 5,800,415 A * | 9/1998 | Olsen | A61F 5/448 |
| | | | 604/338 |
| 5,830,932 A | 11/1998 | Kay | |
| 6,099,508 A * | 8/2000 | Bousquet | A61M 39/0247 |
| | | | 128/DIG. 26 |
| 6,103,803 A | 8/2000 | Cheung et al. | |
| D433,140 S | 10/2000 | Nielsen | |
| 6,197,010 B1 | 3/2001 | Leise et al. | |
| 6,200,261 B1 | 3/2001 | Deininger et al. | |
| 6,210,384 B1 | 4/2001 | Cline | |
| D460,550 S | 7/2002 | Falconer | |
| 6,569,134 B1 | 5/2003 | Leise et al. | |
| 6,635,050 B1 | 10/2003 | Jensen et al. | |
| 6,673,056 B2 | 1/2004 | Metz et al. | |
| 6,790,200 B2 | 9/2004 | Fenton | |
| 6,863,663 B1 * | 3/2005 | Mills | A61F 5/443 |
| | | | 604/337 |
| 6,966,901 B2 * | 11/2005 | Leisner | A61F 5/448 |
| | | | 604/337 |
| D516,212 S | 2/2006 | Persson et al. | |
| 7,049,073 B2 * | 5/2006 | Chernov | C12Q 1/6837 |
| | | | 435/6.12 |
| 7,049,478 B1 | 5/2006 | Smith | |
| D533,660 S | 12/2006 | Persson et al. | |
| 7,214,217 B2 | 5/2007 | Pedersen et al. | |
| 7,374,626 B2 | 5/2008 | Van Der Leden | |
| 7,708,724 B2 * | 5/2010 | Weston | A61M 1/985 |
| | | | 604/304 |
| 7,931,631 B2 | 4/2011 | Pedersen et al. | |
| 8,211,073 B2 * | 7/2012 | Dove | A61F 5/445 |
| | | | 604/338 |
| 8,328,779 B2 | 12/2012 | Fenton | |
| 8,366,695 B2 | 2/2013 | Foley et al. | |
| 8,382,732 B2 | 2/2013 | Oberholtzer et al. | |
| 8,409,157 B2 * | 4/2013 | Haggstrom | A61M 1/985 |
| | | | 604/315 |
| 8,409,158 B2 * | 4/2013 | Edvardsen | A61F 5/443 |
| | | | 604/335 |
| D683,451 S | 5/2013 | Todd et al. | |
| D687,144 S | 7/2013 | Groenberg | |
| D687,145 S | 7/2013 | Groenberg | |
| D699,848 S | 2/2014 | Leroy et al. | |
| 8,652,112 B2 | 2/2014 | Johannison et al. | |
| 8,657,799 B2 | 2/2014 | Carrubba | |
| 8,672,908 B2 | 3/2014 | Todd et al. | |
| 8,708,987 B2 | 4/2014 | Cramer et al. | |
| 8,734,410 B2 * | 5/2014 | Hall | A61M 1/90 |
| | | | 604/319 |
| 8,740,988 B1 | 6/2014 | Hively | |
| 8,758,314 B2 * | 6/2014 | Hall | A61M 1/916 |
| | | | 604/319 |
| 8,771,243 B2 * | 7/2014 | Khan | A61M 1/985 |
| | | | 604/290 |
| 8,834,451 B2 | 9/2014 | Blott et al. | |
| 9,078,990 B1 * | 7/2015 | Obst | A61M 27/00 |
| 9,622,903 B2 * | 4/2017 | Israelson | A61F 5/448 |
| 9,968,480 B2 * | 5/2018 | Nyberg | A61F 5/443 |
| 9,999,537 B2 * | 6/2018 | Ekfeldt | A61F 5/445 |
| 10,335,309 B2 * | 7/2019 | Becker | A61F 5/445 |
| 10,517,754 B2 * | 12/2019 | Praame | A61F 5/443 |
| 11,051,969 B2 * | 7/2021 | Nyberg | A61F 5/445 |
| 2002/0088080 A1 * | 7/2002 | Fenton | A61F 5/445 |
| | | | 604/338 |
| 2003/0088219 A1 * | 5/2003 | Metz | A61F 5/448 |
| | | | 604/339 |
| 2004/0106908 A1 | 6/2004 | Leise et al. | |
| 2005/0054997 A1 * | 3/2005 | Buglino | A61F 5/448 |
| | | | 604/332 |
| 2006/0184145 A1 | 8/2006 | Ciok et al. | |
| 2006/0195053 A1 * | 8/2006 | Oelund | A61F 5/443 |
| | | | 602/42 |
| 2007/0066946 A1 * | 3/2007 | Haggstrom | A61M 1/966 |
| | | | 604/313 |
| 2008/0009779 A1 | 1/2008 | Fabo et al. | |
| 2008/0161778 A1 * | 7/2008 | Steward | A61M 1/74 |
| | | | 604/543 |
| 2008/0287892 A1 * | 11/2008 | Khan | A61M 1/985 |
| | | | 604/289 |
| 2008/0300556 A1 | 12/2008 | Fenton | |
| 2009/0076532 A1 | 3/2009 | Rebuffat et al. | |
| 2009/0131893 A1 * | 5/2009 | Priest | A61F 5/4408 |
| | | | 604/342 |
| 2009/0138030 A1 | 5/2009 | Gronberg | |
| 2009/0192467 A1 * | 7/2009 | Hansen | A61B 17/3462 |
| | | | 604/174 |

(56) References Cited

U.S. PATENT DOCUMENTS

| | | | |
|---|---|---|---|
| 2009/0209917 A1* | 8/2009 | Tanaka | A61M 25/02 604/246 |
| 2009/0216208 A1 | 8/2009 | Leisner | |
| 2009/0234312 A1 | 9/2009 | O'Toole et al. | |
| 2009/0299388 A1 | 12/2009 | Barker et al. | |
| 2009/0312685 A1 | 12/2009 | Olsen et al. | |
| 2010/0022933 A1* | 1/2010 | Oelund | A61F 5/443 604/338 |
| 2010/0145293 A1* | 6/2010 | Verhaalen | A61F 5/445 604/337 |
| 2010/0168693 A1* | 7/2010 | Edvardsen | A61F 5/451 604/355 |
| 2010/0174253 A1 | 7/2010 | Cline et al. | |
| 2010/0174256 A1 | 7/2010 | Rosengren | |
| 2010/0262095 A1* | 10/2010 | Hall | A61M 27/00 604/319 |
| 2010/0280468 A1* | 11/2010 | Haggstrom | A61F 13/0209 604/319 |
| 2010/0324511 A1 | 12/2010 | Dove et al. | |
| 2011/0015475 A1 | 1/2011 | Hanuka et al. | |
| 2011/0071485 A1 | 3/2011 | Foley et al. | |
| 2011/0152987 A1 | 6/2011 | Wahlgren et al. | |
| 2011/0178483 A1 | 7/2011 | Oberholtzer et al. | |
| 2011/0218507 A1* | 9/2011 | Andersen | A61F 5/445 604/338 |
| 2011/0247629 A1* | 10/2011 | Persson | A61M 16/047 128/207.14 |
| 2012/0059341 A1 | 3/2012 | Masters | |
| 2012/0101458 A1* | 4/2012 | Hall | A61M 1/915 604/319 |
| 2012/0143154 A1* | 6/2012 | Edvardsen | A61F 5/4404 604/336 |
| 2012/0143155 A1* | 6/2012 | Edvardsen | A61F 5/443 604/318 |
| 2012/0165767 A1 | 6/2012 | Abrams | |
| 2012/0323193 A1 | 12/2012 | Johannison et al. | |
| 2013/0138063 A1 | 5/2013 | Wiltshire et al. | |
| 2013/0138065 A1 | 5/2013 | Buus | |
| 2013/0192604 A1 | 8/2013 | Persson et al. | |
| 2013/0213415 A1 | 8/2013 | Kay et al. | |
| 2013/0274696 A1 | 10/2013 | Lam | |
| 2013/0304008 A1 | 11/2013 | Hanuka et al. | |
| 2013/0338613 A1* | 12/2013 | Haggstrom | A61M 1/74 604/315 |
| 2014/0114265 A1* | 4/2014 | Israelson | A61F 5/443 604/342 |
| 2014/0148771 A1 | 5/2014 | Luce | |
| 2014/0188090 A1 | 7/2014 | Riesinger | |
| 2014/0213995 A1 | 7/2014 | Garrettson | |
| 2014/0216445 A1 | 8/2014 | Persson | |
| 2014/0276501 A1 | 9/2014 | Cisko | |
| 2014/0276519 A1 | 9/2014 | Luce | |
| 2014/0276526 A1 | 9/2014 | Luce | |
| 2014/0309601 A1* | 10/2014 | Hall | A61F 5/445 604/319 |
| 2014/0316360 A1* | 10/2014 | Ekfeldt | A61F 5/445 604/338 |
| 2015/0297389 A1* | 10/2015 | Nyberg | A61F 5/443 604/344 |
| 2015/0359656 A1* | 12/2015 | Hansen | A61F 5/443 604/344 |
| 2016/0120687 A1* | 5/2016 | Obst | A61M 1/916 604/337 |
| 2016/0302959 A1* | 10/2016 | Kavanagh | A61F 5/449 |
| 2017/0020712 A1* | 1/2017 | Becker | A61F 5/448 |
| 2017/0143535 A1* | 5/2017 | Praame | A61F 5/443 |
| 2017/0224523 A1* | 8/2017 | Bendix | A61F 5/445 |
| 2018/0021164 A1* | 1/2018 | Fenton | A61F 13/02 604/336 |
| 2018/0021165 A1* | 1/2018 | Fenton | A61F 5/445 604/338 |
| 2018/0104089 A1* | 4/2018 | Nyberg | A61F 5/445 |
| 2018/0228641 A1* | 8/2018 | Nyberg | A61F 5/448 |
| 2018/0235801 A1* | 8/2018 | Oellgaard | A61F 5/445 |
| 2020/0046541 A1* | 2/2020 | Sund | A61F 5/445 |

FOREIGN PATENT DOCUMENTS

| | | |
|---|---|---|
| CN | 102215791 A | 10/2011 |
| CN | 203252791 U | 10/2013 |
| DE | 20307688 U1 | 7/2003 |
| EP | 0003671 A1 | 8/1979 |
| EP | 0228191 A2 | 7/1987 |
| EP | 0317326 A2 | 5/1989 |
| EP | 0413250 A1 | 2/1991 |
| EP | 0415592 A2 | 3/1991 |
| EP | 0519586 A1 | 12/1992 |
| EP | 0700777 A1 | 3/1996 |
| EP | 0882437 A2 | 12/1998 |
| EP | 0894482 A2 | 2/1999 |
| EP | 0963743 A2 | 12/1999 |
| EP | 1053725 A1 | 11/2000 |
| EP | 1163892 A2 | 12/2001 |
| EP | 1178766 A1 | 2/2002 |
| EP | 1464308 A1 | 10/2004 |
| EP | 1541180 A2 | 6/2005 |
| EP | 2012718 A1 | 1/2009 |
| EP | 2371920 A1 | 10/2011 |
| FR | 1345339 A | 12/1963 |
| FR | 2721204 A1 | 12/1995 |
| GB | 0249897 A | 4/1926 |
| GB | 0874705 A | 8/1961 |
| GB | 2230017 A | 10/1990 |
| GB | 2311467 A | 10/1997 |
| GB | 2509752 A | 7/2014 |
| HU | 190848 B | 11/1986 |
| HU | 200875 A2 | 7/2002 |
| HU | 0200875 A2 | 7/2002 |
| JP | 09-220247 A | 8/1997 |
| JP | 10-192318 A | 7/1998 |
| JP | 10-272742 A | 10/1998 |
| JP | 11-290364 A | 10/1999 |
| JP | 2000-107217 A | 4/2000 |
| JP | 2001-523517 A | 11/2001 |
| JP | 2003-038541 A | 2/2003 |
| JP | 2003-126133 A | 5/2003 |
| JP | 2003-290265 A | 10/2003 |
| JP | 2004-298624 A | 10/2004 |
| JP | 2007-105474 A | 4/2007 |
| JP | 2008-526354 A | 7/2008 |
| JP | 2012-511972 A | 5/2012 |
| JP | 2014-069061 A | 4/2014 |
| JP | 2014-079548 A | 5/2014 |
| JP | 2015-000327 A | 1/2015 |
| RU | 2220685 C1 | 1/2004 |
| RU | 2012104006 A | 8/2013 |
| WO | 93/04646 A1 | 3/1993 |
| WO | 93/18725 A1 | 9/1993 |
| WO | 94/18919 A1 | 9/1994 |
| WO | 95/20927 A1 | 8/1995 |
| WO | 95/24169 A1 | 9/1995 |
| WO | 98/17329 A1 | 4/1998 |
| WO | 98/53771 A1 | 12/1998 |
| WO | 99/11302 A1 | 3/1999 |
| WO | 99/26565 A1 | 6/1999 |
| WO | 00/53133 A1 | 9/2000 |
| WO | 01/05340 A2 | 1/2001 |
| WO | 01/35875 A2 | 5/2001 |
| WO | 03/75808 A1 | 9/2003 |
| WO | 2006/038025 A1 | 4/2006 |
| WO | 2006/075948 A1 | 7/2006 |
| WO | 2007/121744 A1 | 11/2007 |
| WO | 2008/031411 A1 | 3/2008 |
| WO | 2009/006900 A1 | 1/2009 |
| WO | 2009/006901 A1 | 1/2009 |
| WO | 2009/023870 A1 | 2/2009 |
| WO | 2010/054662 A2 | 5/2010 |
| WO | 2010/060116 A1 | 5/2010 |
| WO | 2010/069334 A1 | 6/2010 |
| WO | 2011/003420 A1 | 1/2011 |
| WO | 2011/050816 A1 | 5/2011 |

(56) References Cited

FOREIGN PATENT DOCUMENTS

| | | |
|---|---|---|
| WO | 2011/108972 A1 | 9/2011 |
| WO | 2011/129738 A1 | 10/2011 |
| WO | 2012/022352 A1 | 2/2012 |
| WO | 2012/079592 A1 | 6/2012 |
| WO | 2012/150235 A1 | 11/2012 |
| WO | 2013/009848 A2 | 1/2013 |
| WO | 2014/081889 A1 | 5/2014 |
| WO | 2014/086369 A1 | 6/2014 |
| WO | 2015/090332 A1 | 6/2015 |

* cited by examiner

METHOD OF PROVIDING AN OSTOMY DEVICE THAT IS SHAPE-ADJUSTABLE TO CONFORM TO A BULGE OR A HERNIA ASSOCIATED WITH A STOMA Disclosed is an adaptable ostomy base plate for attachment to a skin surface of a user and a collecting bag connected to the adhesive base plate. The adaptable base plate includes a top film, an adhesive composition, and at least one release liner.

BACKGROUND

In connection with surgery for a number of diseases in the gastro-intestinal tract, one of the consequences in many cases is that the patient is left with an abdominal stoma, such as a colostomy, an ileostomy or a urostomy, in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time. Ostomy appliances are typically attached to the skin of the ostomy user by means of an adhesive wafer on the ostomy appliance.

DETAILED DESCRIPTION OF THE INVENTION

Figure 1:
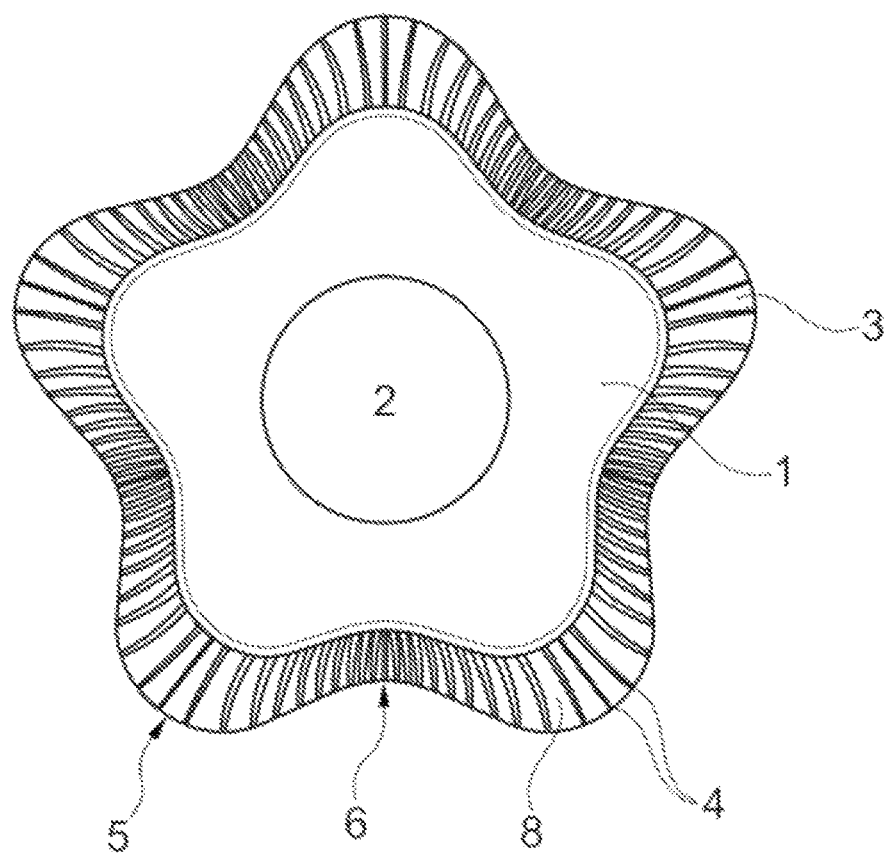
In FIG. 1 is shown an adaptable base plate,
In FIG. 2 is shown a cross-section of an adaptable base plate in concave configuration,
In FIG. 3 is shown a cross-section of an adaptable base plate in convex configuration.

Embodiments (see FIGS. 1-3) provide an adaptable ostomy base plate 90 comprising a flexible top film 92, having a first section 101 and a second section 103, and having at least a first elastic skin-friendly adhesive 94 on a proximal surface 96 of said flexible top film, a stoma-receiving through-going hole 102 defining an inner boundary in said first section, said first section being adjacent to and extending radially from said through-going hole and said second section surrounding said first section defining an outer boundary of the base plate, and one or more release liners, the base plate has a substantially convex shape for initial engagement with a peristomal skin surface, the base plate being invertible to a substantially concave shape to fittingly engage to a topography of the peristomal skin surface for permanent engagement thereto and wherein said second section of the base plate is in the form of a plurality of petals extending away from the central area; and a plurality of bridges, each bridge formed between adjacent petals of the plurality of petals.

For interpretations in the context of the present application, some definitions regarding the subject matter of the attached claims are presented below.

When referring to the proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction, or axially, is defined as the direction of the stoma when the appliance is worn by a user. Thus, the axial direction is substantially perpendicular to the abdominal surface of the user.

The radial direction, or radially, is defined as transverse to the axial direction that is transversely to the direction of the stoma.

An "adaptable ostomy base plate" is intended to define that at least a part of the ostomy base plate can change its form or shape by an intended interaction of a user or health care professional.

A "flexible top film" is intended to define a film material carrying or having disposed thereon, adhesive material to make the product adhere to the skin of a user and that the top film material does not break or become weaker even at very high elongation or stretching rates. A flexible top film is further defined below.

An "elastic skin-friendly adhesive" is intended to define an adhesive material having a low risk of irritating the skin of a user and that the adhesive material is capable of following the elongations and relaxations of the flexible top film without breaking or substantially changing characteristics. An elastic skin-friendly adhesive is further defined below.

An "adhesive base plate" is intended to define a top film coated on the proximal surface with a skin-friendly adhesive.

A "substantially convex shape" is intended to define that an element or its corresponding surface has a shape or form that provides an overall convexity. In other words, while a smaller section or zone making up part of the overall element or its corresponding surface may have e.g. a linear shape or form, the element or surface as a whole has a convex shape. It is of course to be understood that if for a sheet- or plate-like element one major surface has a convex shape, the opposite major surface may necessarily have a corresponding concave shape. However, for clarification purposes only, and in relation to the present application, "convex" may preferably refer to the proximal side and "concave" to the distal side as both defined above.

Similarly, a "substantially concave shape" is intended to define that an element or its corresponding surface has a shape or form that provides an overall concavity.

"Initial engagement" is intended to define the first contact between the ostomy base plate and the skin surface of the user in the process of applying the product; however not meaning that the ostomy base plate is fully and functionally correct attached to the skin surface.

"Permanent engagement" is intended to define the engagement or attachment of the ostomy base plate when the application process is completed and the ostomy base plate is fully and functionally correct attached to the skin surface. However, it should be understood that permanent engagement is only intended to mean for the normal life- or wear time of the ostomy base plate.

"Release liner" is intended to define a liner covering the proximal (skin contacting) side of the skin-friendly adhesive, that ensures at least that the properties of the adhesive are preserved and that the adhesive surface is not laid open until just before the use.

"Fittingly engage" is intended to define that the attachment between the ostomy base plate and the skin surface is as good as possibly feasible and at least with no or only insignificant creases or folds on the proximal surface of the base plate.

"Peristomal skin surface" is intended to define an area of the skin surface adjacent to and surrounding the stoma. The extent of the area may be considered to correspond approximately to a skin surface area covered by at least a first section of the ostomy base plate—the first section then being closer to the stoma than a second section.

"Invertible" is intended to define that the at least first and/or second section provides little or no resistance to being shifted from a substantially convex shape to a substantially concave shape, or vice versa, by a movement involving no sudden switching or "flipping-over" of the section (i.e. as it is known from a bi-stable construction which may change shape when a certain force-threshold is reached).

"Store configuration" is intended to describe the position of the base plate before application is completed. The base plate is stable in this configuration and can be stored in this configuration. In the initial steps of application, the base plate may be in store configuration.

"Use configuration" is intended to describe the position of the base plate after application is completed, and is the inverted configuration of the store configuration.

"Petal" is intended to describe a radially outwardly extending part of the base plate, it can be pointy with an apex or it may be more rounded like the leaf of a flower.

The combined features of the baseplate being soft, curved, and invertible and being provided with radially extending petals along the edge portion facilitates a base plate being highly adaptable to a stoma on a bulge or hernia. The curved shape together with the softness/elasticity enables a snug fit around the bulge or hernia and the petals allow for fitting to different shapes and diameters of the bulge or hernia, with a minimum of folds and wrinkles, thereby decreasing the risk of leakage. Furthermore, the plate being invertible enables easy and precise application of the plate.

The outer boundary of the base plate is defined by the petal of the second section of the base plate. Thus, the outline of the base plate may appear as star or flower shaped. The base plate may comprise at least three petals, such as four petals, such as five petal or even such as six petals, such as 7 petals, such as 8 petals, such as 9 petals or even at least 10 petals.

The petals may be equidistantly spaced apart around the circumference of the central part.

The petals facilitates tailor fitting the base plate to the bulgy peristomal skin with decreased amount of folds and wrinkles compared to a plate without petals.

The outer periphery of the base plate may be provided with embossed lines 98. The embossed lines may be located to parts of the periphery such as the bridges or petals or the embossed lines may be applied to the entire periphery of the base plate. The embossed lines provides increased flexibility to the base plate as well as it reduces the risk of folds and wrinkles of the peripheral portion of the base plate. The embossed lies may be located where folding lines may naturally occur, thereby absorbing the forces of the folds.

The at least one release liner may be form stable and able to fix the concave contour of the base plate. Due to the elasticity of the base plate, it may be advantageous to have a release liner that is able to keep the base plate in shape until application.

The release liner may be produced from a material that can be thermo formed. The release liner may have a stiffness being higher than the stiffness of the combined top film and adhesive layer. The release liner may have a thickness of 0.10 to 0.20 mm, more preferred 0.15 mm. The release liner may have a thickness of 0.15 mm.

The at least one release liner used in connection with the ostomy base plate may suitably be a siliconised or fluorinated liner, such as a siliconised or fluorinated craft paper, polyethylene, polypropylene or polyethylene terephthalate film.

The adaptable base plate may be provided with a collection bag. The collection bag may be attached permanently to the base plate, being a one-piece ostomy appliance or it may be detachable, being a two-piece ostomy appliance.

The ostomy base plate may be provided with coupling means for attachment of a collection bag. The coupling means may be in the form of a mechanical coupling or it may be an adhesive coupling.

An ostomy device with an adaptable base plate and a collection bag permanently attached thereto, a so-called one-piece device, may be very soft and it can be difficult to maintain the convex shape of the base plate when the release liner is removed. In order to stabilize the device, it may be provided with a reinforcing structure.

The ostomy base plate may be provided with a reinforcement structure. The reinforcing structure may be arranged in a radial direction between the inner and outer radial boundary of the base plate. The reinforcing structure may stabilise the base plate and prevent deformation of the stoma-receiving opening in the longitudinal and/or the axial direction during use.

In embodiments, the reinforcing structure is arranged in an axial direction between the proximal surface and the distal surface.

In embodiments, the reinforcement structure is arranged on a distal surface of the top film.

The reinforcing structure may be in the form of a closed line shape, such as a ring, an ellipse or a polygon.

The reinforcing structure may be ring shaped flange.

In embodiments, the reinforcing structure defines the boundary between the first and the second section of the base plate.

In embodiments, the reinforcement structure may be embedded within the top film of the ostomy base plate.

The reinforcement structure may be positioned at a radial distance from the stoma receiving opening of 0-50% of the radial distance from the inner boundary to the outer radial boundary, or more specifically between 1-40% of the radial distance from the inner boundary to the outer radial boundary, or even more specifically between 2-30% of the radial distance from the inner boundary to the outer radial boundary, or especially between 5-20% of the radial distance from the inner boundary to the outer radial boundary. The outer radial boundary of the base plate is herein defined as the shortest radius measured of the outer boundary of the base plate, being at the bridges.

The reinforcement structure may be made of a material that is more rigid than the adhesive layer and/or the top film. The reinforcement structure may be made of a thermoplastic material, a metallic material, a woven material, a non-woven material, a fibrous material or any material combination thereof.

The reinforcement structure may be made of a material that provides a greater rigidity along the radial axis than the adhesive and/or top films of the ostomy base plate. The reinforcement structure may be made of a material and have a construction that provides a greater rigidity along the axial direction than the adhesive and/or top films of the ostomy base plate.

The reinforcement structure facilitates that the base plate maintains a convex shape when the release liner is removed.

In embodiments the width of the reinforcement structure may be approximately 4-10 mm, such as 4-8 mm, such as 5-7 mm or even such as 5.5 mm. In a two-piece ostomy appliance, the reinforcing structure may be combined with a coupling for attachment of a collection bag. In such cases, the structure may be broader, up to 11 mm. The reinforcing structure has an inner radial periphery and an outer radial periphery, the width of the reinforcing structure being defined as the radial distance between the inner and outer periphery.

In embodiments, the reinforcing structure may be attached to the distal surface of the base plate along the outer periphery of the structure, leaving the inner periphery unattached, allowing the adhesive wafer to stretch and compact more freely under the structure.

The concave/convex shape of the base plate may be a section of a sphere. This facilitates easy fitting to a protruding stoma. The curvature of the central portion of the base plate may fit to the curved body part and the petals along the outer boundary may allow tailor fit to the peripheral area of the body part. Compared to flat devices, the risk of folds and wrinkles (and thereby risk of leakage and discomfort) are decreased by having a base plate being curved in a shape that substantially matches the peristomal area when the stoma is located on a bulge.

By the invention according to the first aspect, a number of advantageous effects are achieved. First, a user having a stoma located on a bulge or hernia, or on an otherwise "hilly" topographic skin surface, has improved control of the product application procedure.

This effect is at least partly achieved in the following manner: subsequent to removal of at least one release liner covering at least partly the first section, the user engages a part of the first section immediately adjacent the stoma-receiving through-going hole with the peristomal skin surface, whereby only a small area of the adhesive on the proximal surface of the flexible top film is engaged with the peristomal skin surface.

Thereby, the user is provided with the opportunity to correct the positioning of the ostomy base plate to a more suitable position in case of misalignment of the initial engagement without having engaged the whole of the proximal adhesive surface of the flexible top film with the skin surface. This may be particularly advantageous in cases where the user has limited or no visual contact with the stoma.

Furthermore, since at least the first section has a first substantially convex shape, a user reaching down to the stoma located on the bulge or hernia in order to apply the product will have improved tactile and/or visual contact with the stoma and/or the peristomal area. This is because the part of the first section not initially engaging the peristomal skin surface extends away from the skin surface, thus leaving some space between the base plate and the skin, giving room for one or more of the user's fingers, and thereby the first section also does not block or impede possible visual contact for correct positioning of the base plate in relation to the stoma.

Once the initial engagement of the first section is effected, the base plate is inverted by the user to a substantially concave shape to fittingly engage the first section with the peristomal skin surface on the bulge or hernia.

It is important to understand the manner in which this is done. Due to the flexibility of the flexible top film and the elasticity of the skin-friendly adhesive, the adhesive proximal side of the first section will adapt smoothly to the topography of the peristomal skin surface when the user applies a gentle pressure to the distal surface of the first section.

This may advantageously, but not exclusively, be done by the user letting his finger or fingers describe one or more radial motions by placing the finger(s) immediately adjacent the stoma, providing pressure to the distal surface, and sliding the finger gently across the distal surface of the first section radially away from the stoma. Alternatively, the adaptation may be done by a motion placing a finger immediately adjacent the stoma, providing pressure to the distal surface, and sliding the finger gently in a "spiral-like" pattern gradually away from the stoma over the entire distal surface of the first section.

However, regardless of the way of adaptation, at least the flexibility of the flexible top film and the elasticity of the skin-friendly adhesive along with the first substantially convex shape of the first section make the fitting engagement of the first section possible.

Then the petals of the second section is attached to the skin. The petal allows a custom fit to the bulge or hernia as they can adapt the base plate to a curve with a slightly smaller radius than the plate as well as it is able to cope with a broader basis for the bulge/hernia without tightening.

As can be understood from the above, the flexible top film and the elastic skin-friendly adhesive facilitate the inversion of the first section for application to the peristomal skin surface by a continuous, regular movement. This provides a user with improved control of the application procedure. This should be seen in contrast to a sudden movement which would be the case e.g. in the case of a bi-stable construction, i.e. a construction having one predetermined position where it changes shape from one form to another, e.g. from convex to concave.

The flexible top film according to the invention may be a blown film primarily based on one or more Ethylene Vinyl Acetate (EVA) materials, one or more thermoplastic polyurethane elastomer (TPU) based materials and one or more polyethylene (PE) materials.

Particularly, but not exclusively, the EVA and TPU based materials may provide a good basis for engagement of the top film with other elements of the ostomy base plate such as the adhesive(s) and optional first coupling means, or in the case of the base plate being used for a one-piece ostomy appliance, with the material of the collecting bag for human body wastes. The PE material(s) may particularly, but not exclusively, provide a suitable basis for shaping the flexible top film into a convex or concave shape to be able to fittingly engage with a topography of a user's skin surface.

In embodiments, the flexible top film is a three-layer laminate.

Particularly, but not exclusively, the flexible top film may be made as a laminate comprising three individual (blown) layers each of which is made from either EVA, TPU or PE or from a blend of these. In the three-layer laminate, the distal-most (with reference to the use situation of the ostomy base plate) layer may be made from a blend of Elvax® 3190, an EVA material from DuPont, and Orevac® 18360, a PE material from Arkema; the middle layer may be made from a blend of Elvax® 3190, Elastollan® 890, a TPU-Polyester material from BASF and Elastollan® 978, another TPU-Polyester material from BASF and; the proximal layer may also be made from a blend of Elvax® 3190, Elastollan® 890 and Elastollan® 978. In addition to these components each of the distal and proximal layers of the three-layer laminate may also comprise a minor amount of slip agent (to assist when unrolling the top film material for production of the ostomy base plate). The slip agent may be a PE/EVA polymer carrier containing silica, oleamid (fatty acid oleic acid) and erucamide (monounsaturated omega-9 fatty acid), such as Polystatic® 90200-2. The silica and the ole-/erucamides in the slip agent provide the slipping effect.

The overall thickness of the flexible top film may be in a range of 30-70 µm, such as 35-50 µm, such as approximately 40 µm. In embodiments of the three-layer laminate, each individual layer may have a thickness of at least 10 µm for ease of production of the individual layers.

The flexible top film may be stretched prior to being used in the production of the ostomy base plate. This will provide a pre-tensioning or bias in the flexible top film. The flexible top film may be stretched radially in all directions to obtain the same bias in all directions of the plane thereof. This pre-tensioning or bias in the flexible top film incurs additional flexibility to the flexible top film. Particularly, it may improve the film's ability to adapt to a certain shape in a shaping process.

The flexible top film may have a flexibility measured as a percentage of elongation of the flexible top film material before it fails (considered as the point where plastic deformation of the flexible top film occurs). The flexible top film may be 250-700% elongatable, such as 300-600% elongatable, such as 350-450% elongatable, such as 400% elongatable before failure.

The first elastic skin-friendly adhesive according to the invention may be any pressure sensitive adhesive composition suitable for medical purposes. It may comprise a rubbery elastomeric base and one or more water soluble or water swellable hydrocolloids, the adhesive composition comprising a substantially homogeneous mixture of 25-60% of one or more polyisobutylenes, 3-35% of one or more styrene copolymers, and 20-60% of one or more hydrocolloids, wherein the percentage by weight of one or more polyisobutylenes and one or more styrene copolymers and one or more hydrocolloids add up to 100% by weight of the adhesive composition. For further information on such compositions, reference is made to applicant's granted European patent EP1541180B1.

The thickness of the first elastic skin-friendly adhesive layer may be in a range of 1-2 mm, corresponding to 1000 µm-2000 µm, such as 1200 µm-1800 µm, such as 1400 µm-1600 µm.

For the production of the ostomy base plate, the following is an example of manufacture: first the adhesive(s) is/are provided on the proximal surface of the flexible top film and thereafter the at least one release liner is provided on the adhesive surface. At least the first section of the planar laminate blank is then subsequently placed in a vacuum-forming machine, the moulding tool having the relevant convex form. Heating means, such as a radiant heat source is placed in connection with the vacuum-forming machine in order to soften the laminate blank, and the laminate blank is subjected to heat and vacuum forming for an adequate holding time. Alternatively, the laminate blank may also be manufactured by means of a heat and pressure die or indeed any other suitable procedure.

Due to its elasticity, the first skin-friendly adhesive may easily adapt to the convex shape of at least the first section together with the flexible top film and the at least one release liner in the shaping process. Indeed, subjected to the above described shaping process, at least the first section of the ostomy base plate according to the invention initially always has the convex shape notwithstanding its high degree of adaptability. As mentioned, this may be seen in contrast to e.g. the known bi-stable convex ostomy products that are relatively rigid and only adaptable in an "either inverted/not inverted" sense.

The second section may be permanently engaged to the skin surface of the user by fitting each petal to the skin. The engagement of the second section to the skin surface may be carried out after the first section has been permanently engaged with the peristomal skin surface.

The second section surrounds the first section of the adaptable ostomy base plate.

In embodiments, the adaptable ostomy base plate comprises a second skin-friendly adhesive on the proximal surface of the flexible top film.

The second skin-friendly adhesive may be provided so as to give the proximal surface of the base plate different characteristics and/or effects. As an example, the second skin-friendly adhesive may comprise smaller or a larger amount of a moisture absorbing component such as hydrocolloids and/or be more or less adaptable than the first skin-friendly adhesive. The second skin-friendly adhesive may be provided in a single or in multiple zones or areas. The zones or areas may have particular suitable shapes or forms depending on the function or effect of the second skin-friendly adhesive.

In embodiments, the first elastic skin-friendly adhesive is provided on the first section and the second skin-friendly adhesive is provided on the second section.

This disposition of the first and second skin-friendly adhesive effectively provides an ostomy base plate wherein the first skin-friendly adhesive having one set of characteristics covers the peristomal area, and the second skin-friendly adhesive having another set of characteristics covers the skin surface around (radially beyond) the peristomal skin surface.

In embodiments, the second skin-friendly adhesive is elastic. This means, that in addition to the first elastic skin-friendly adhesive, also the second skin-friendly adhesive has elastic properties. The second skin-friendly adhesive may be more or may be less elastic than the first elastic skin-friendly adhesive or the two adhesives may even have identical elasticities if desired.

Where the elasticity of a construction is typically measured by the tensile elasticity Modulus (E) (also known as Young's Modulus) the elasticity of an adhesive is typically measured by the shear Modulus (G).

The shear Modulus of a viscoelastic material like an adhesive can be divided into a viscous part called the Loss Modulus (G") and an elastic part called the Storage Modulus (G'). The elastic response of the adhesives can therefore be measured by measuring G' by dynamic mechanical analysis (DMA), which is a well-known and established procedure to a skilled person working in the field of adhesives.

Body movements according to normal daily life routines typically occur at frequencies around 1-10 Hz. At these frequencies, the G' of the first elastic skin-friendly adhesive may be in a range from 850-1200 MPa, whereas G' of the second elastic skin-friendly adhesive may be in a range from 40-80 MPa.

In embodiments, the second elastic skin-friendly adhesive comprises a polar plasticising oil or a combination of polar plasticising oils in the content of above 10% (w/w) of the final second adhesive, and at least one polar polyethylene copolymer, wherein the content of the polyethylene copolymer is 10-50% (w/w) of the final second adhesive, the polyethylene copolymer has a melt flow index below 2 g/10 min (190° C./21.1N).

Polymers that may be used for the second skin-friendly adhesive will generally be copolymers of ethylene and a polar monomer. The copolymers typically comprise less than about 70% ethylene, have water vapour transmission of more than 50 g/m2/day and a melt flow index of less than 2 g/10 min (190° C./21.1N). The melt flow index can be measured by the methods given in ISO 1133 and ASTM D1238. Examples of such polymers are copolymers of ethylene and vinyl acetate and copolymers of ethylene and butyl acrylate. Particularly preferred is ethylene and vinyl acetate copolymers with more than about 40% (w/w) vinyl acetate, a melt flow index of less than 2 g/10 min (190° C./21.1N), and a water vapour transmission of more than 50 g/m2/day for a 150 μm sheet when measured ac-cording to MVTR Test Method (inverted cup method).

Further information on the types of adhesives suitable for the second skin-friendly adhesive disclosed in these embodiments is available in applicant's published application WO 2009/006901A1.

In embodiments, the thickness of the second elastic skin-friendly adhesive is 300-700 μm, such as 550-650 μm, such as 600 μm.

In embodiments, the adhesive base plate will have a proximal ("skin-facing") surface, which faces the skin of the user during use, and a distal ("non-skin-facing") surface, which faces away from the user's skin during use. Before use, the proximal surface of the adhesive base plate can be covered by a release liner, which is releasably attached to the adhesive. The release liner can be removed by the user immediately prior to application of the adhesive base plate to the skin. Both before and during use, the distal surface of the adhesive base plate can be made up of a top film, which can be used to attach the collecting bag to the adhesive base plate, for instance by welding.

The adhesive base plate may include an absorbent adhesive composition. The absorbent adhesive composition is capable of absorbing moisture. The purpose of having an absorbent adhesive composition as a part of an ostomy device is to allow the absorbent adhesive composition to absorb moisture produced by the skin and thereby prevent accumulation of moisture at the skin surface, underneath the ostomy device. Accumulation of moisture on the skin surface can lead to damage of the skin, such as maceration.

In an aspect the invention relates to an ostomy appliance comprising a collection bag and an adaptable ostomy base plate comprising a flexible top film, having a first section and a second section, and having at least a first elastic skin-friendly adhesive on a proximal surface of said flexible top film, a stoma-receiving through-going hole defining an inner boundary in said first section, said first section being adjacent to and extending radially from said through-going hole and said second section surrounding said first section defining an outer boundary of the base plate, and one or more release liners, the base plate has a substantially convex shape for initial engagement with a peristomal skin surface, the base plate being invertible to a substantially concave shape to fittingly engage to a topography of the peristomal skin surface for permanent engagement thereto and wherein said second section of the base plate is in the form of a plurality of petals extending away from the central area; and a plurality of bridges, each bridge formed between adjacent petals of the plurality of petals, wherein the collection bag is detachable from the base plate.

In an aspect the invention relates to an ostomy appliance comprising a collection bag and an adaptable ostomy base plate comprising a flexible top film, having a first section and a second section, and having at least a first elastic skin-friendly adhesive on a proximal surface of said flexible top film, a stoma-receiving through-going hole defining an inner boundary in said first section, said first section being adjacent to and extending radially from said through-going hole and said second section surrounding said first section defining an outer boundary of the base plate, and one or more release liners, the base plate has a substantially convex shape for initial engagement with a peristomal skin surface, the base plate being invertible to a substantially concave shape to fittingly engage to a topography of the peristomal skin surface for permanent engagement thereto and wherein said second section of the base plate is in the form of a plurality of petals extending away from the central area; and a plurality of bridges, each bridge formed between adjacent petals of the plurality of petals, wherein the collection bag is integrated with the base.

In embodiments, the second absorbent adhesive composition is located only in the central part of the adhesive base plate. The absorbent adhesive composition may be located as a substantially ring-shaped element in the central part of the adhesive base plate, thus surrounding the stoma during use.

The release liner may be of any material known to be useful as a release liner for medical devices. For instance, the release liner may be in the form of a polymer film, foil, or paper, having release properties that enable the adhesive to be released easily from the liner. Such properties may be inherent in the material or the layer may be siliconized, coated with a low surface tension coating, or subjected to other appropriate surface modifications. Release liners are in general made on a mechanically stiff backing such as paper, polyethylene, polypropylene, or polyethylene terephthalate. This stiffness will support the adhesive base plate when applying the collecting device.

In embodiments, the second absorbent adhesive composition is in the form of a ring-shaped adhesive element located around the hole in the adhesive base plate and in contact with the release liner. Such a ring-shaped absorbent adhesive element could have a diameter of 30-70 mm, such as 40-70 mm, such as 50-70 mm, such as 60-70 mm. The ring-shaped adhesive element could for instance have a diameter of 30 mm, 40 mm, 50 mm, 60 mm, or 70 mm. The ring shaped element could have a width, i.e. the distance from the inner rim of the ring to the outer rim of the ring measured along the surface of the ring, of at least 10 mm, at least 20 mm, at least 30 mm, at least 40 mm, at least 50 mm, 10-20 mm, 10-30 mm, 10-50 mm, 20-30 mm, 20-40 mm, 20-50 mm, 30-40 mm, 30-50 mm, or 40-50 mm. The width of the element can be constant over the entire element or it may vary.

An adhesive element could also have an only roughly ring-shaped, oval, or roughly oval form. In that case, the mentioned diameters would be the maximum distance from one point on the outer edge of the element to another point on the outer edge of the element.

In embodiments, the second absorbent adhesive composition comprises a polymer comprising monomer units selected from the group consisting of styrene, isoprene, butadiene, ethylene, and butylene.

In embodiments, the second absorbent adhesive composition comprises a styrene block co-polymer.

In embodiments, the second absorbent adhesive composition comprises a styrene block co-polymer selected from the group consisting of styrene-isoprene-styrene (SIS), styrene-butadiene-styrene (SBS), styrene-isobutylene-styrene (SIBS), and styrene-ethylene/butylene-styrene (SEBS).

In embodiments, the second absorbent adhesive composition comprises a polyethylene copolymer.

In embodiments, the second absorbent adhesive composition comprises a polyethylene copolymer selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

In embodiments, the second absorbent adhesive composition comprises polyisobutylene (PIB).

In embodiments, the second absorbent adhesive composition comprises absorbent material selected from the group consisting of hydrocolloids, microcolloids, salt, and super absorbent particles.

In embodiments, the absorbent adhesive composition comprises an absorbent material in an amount of 1-60% (w/w) of the composition.

For instance, the absorbent adhesive composition comprises an absorbent material in an amount of 1-40% (w/w) or 1-20% (w/w) or 20-40% (w/w) or 20-60% (w/w) or 40-60% (w/w) or 25-50% (w/w) of the composition.

In embodiments, the absorbent material is selected from hydrocolloid, water soluble salt, mono, di- and oligosaccharides, sugar alcohols, polypeptides, organic acids, inorganic acids, amino acids, amines, urea, super absorbent particles such as polyacrylic acid, glycols such as polyethylene glycol, fumed silica, bentone, bentonite, and mixtures thereof.

In embodiments, the hydrocolloid is selected from guar gum, locust bean gum, pectin, potato starch, alginates, gelatine, xantan or gum karaya, cellulose derivatives, salts of carboxymethyl cellulose, sodium carboxymethyl cellulose, methyl cellulose, hydroxypropyl cellulose, hydroxyethyl cellulose, sodium starch glycolate, polyvinylalcohol, and mixtures thereof.

In embodiments, the water soluble salt is selected from NaCl, $CaCl_2$, $K_2SO_4$, $NaHCO_3$, $Na_2CO_3$, KCl, NaBr, NaI, KI, $NH_4Cl$, $AlCl_3$, $CH_3COONa$, $CH_3COOK$, HCOONa, HCOOK, and mixtures thereof.

In embodiments, the switchable and/or the absorbent adhesive composition may comprise ingredients such as tackifiers, extenders, non-reactive polymers, oils (e.g. polypropyleneoxide, ethyleneoxide-propyleneoxide copolymers, mineral oil), plasticizers, fillers, and surfactants.

DETAILED DESCRIPTION OF THE DRAWINGS

In FIG. 1 is shown a top view of an embodiment of the adaptable base plate 90, the plate comprising a first central portion 1, or first section 101, surrounding a stoma-receiving hole 2, 102 and a second peripheral portion 3, or second section 103. The peripheral portion is provided with bevelled lines 4 extending radially along the edge portion. The outer boundary of the base plate is defined by radially extending petals 5 interconnected by bridges 6.

Figure 2:
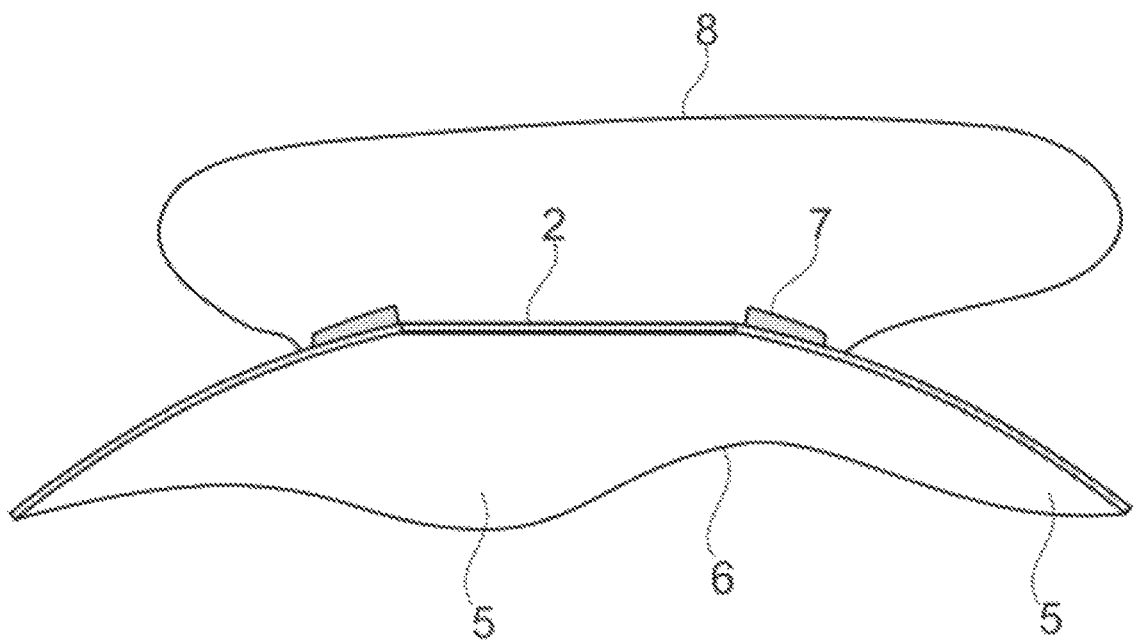

In FIG. 2 is shown a cross section of a base plate with a reinforcing structure 7 in the form of a ring of stiffer material. The reinforcing structure 7 is in the form of a flange being coaxial to the central hole. A collection bag 8 is attached to the base plate. The base plate is shown in its concave configuration as if applied to the skin of a user where the petals 5 are fitted to the skin of the user.

Figure 3:
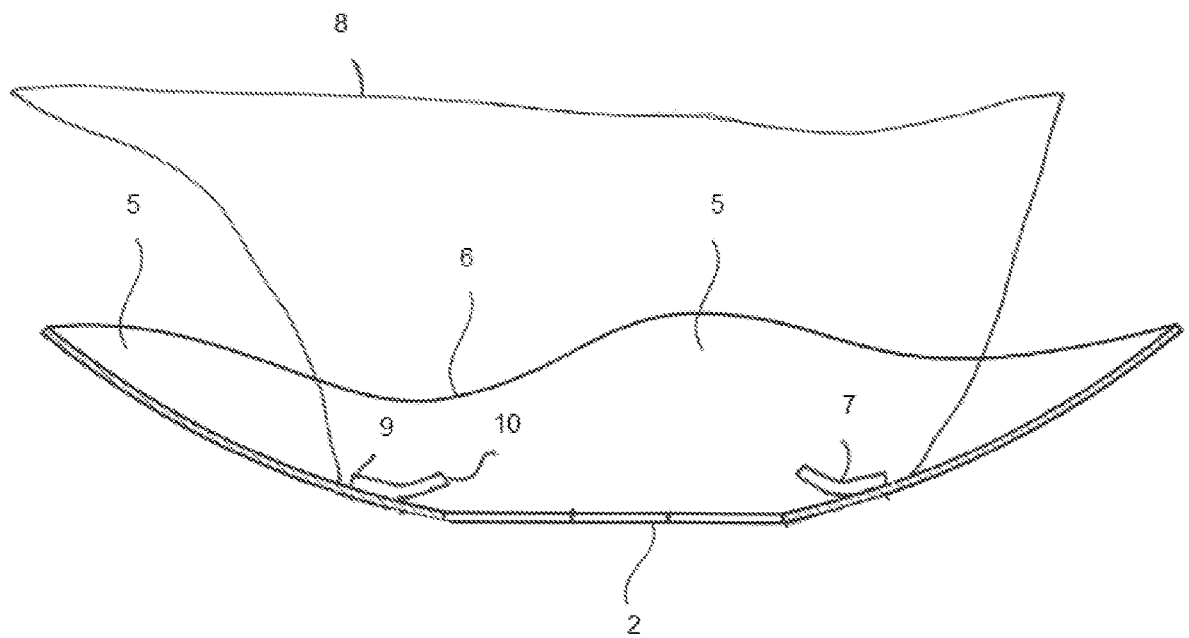

In FIG. 3 is shown an embodiment of the adaptable base plate in its convex configuration. The reinforcing structure 7 is in the form of a flange being attached to the distal surface of the base plate along the outer periphery 19 of the flange, leaving the inner periphery 10 of the flange unattached. The inner periphery 10 of the flange may thus be able to be distanced from the base plate when the plate is in the convex configuration thereby allowing more stretchability of the base plate underneath the flange. When the base plate is inverted to the concave configuration during application, the entire flange may be in contact with the distal surface of the base plate, thereby stabilising the plate in this configuration.

What is claimed is:

1. A method of providing a user or a healthcare worker with an ostomy device that is shape-adjustable to conform to skin around a stoma associated with a bulge or a hernia, the method comprising:
   providing the user or the healthcare worker with: an adaptable ostomy base plate comprising a film having a distal surface that defines a distal side of the adaptable ostomy base plate and a first adhesive on a proximal surface of the film such that the first adhesive forms a proximal side of the adaptable ostomy base plate, and a reinforcing structure comprising an outer radial periphery attached to the distal surface of the film and an inner radial periphery unattached to the distal surface of the film;
   delivering the adaptable ostomy base plate to the user or the healthcare worker in a storage configuration characterized by the first adhesive and the proximal side of the adaptable ostomy base plate each in a substantially convex shape; and
   configuring the adaptable ostomy base plate for inverting from the storage configuration to a use configuration upon inverting the substantially convex shape of the first adhesive and the proximal side of the adaptable ostomy base plate to a substantially concave shape and stabilizing the adaptable ostomy base plate in the use configuration by contacting the inner radial periphery of the reinforcing structure with the distal surface of the film.

2. The method of claim 1, further comprising providing the user or the healthcare worker with the adaptable ostomy base plate having a stoma-receiving hole formed in a first section that is adjacent to and extends radially from the hole to a second section surrounding the first section; a plurality of petals extending away from the first section; and a plurality of bridges, with each bridge formed between one petal and an adjacent petal of the plurality of petals.

3. The method of claim 1, further comprising providing a release liner removably secured to the first adhesive on the proximal surface of the film.

4. The method of claim 1, further comprising providing a release liner removably secured to the first adhesive on the proximal surface of the film and configuring the release liner to have a stiffness larger than a combined stiffness of the first adhesive and the film.

5. The method of claim 1, further comprising providing a release liner removably secured to the first adhesive on the proximal surface of the film and configuring the release liner to be form-stable and adapted to keep the adaptable ostomy base plate in the storage configuration until application.

6. The method of claim 1, further comprising providing an entirety of an outer boundary of the adaptable ostomy base plate with embossed lines.

7. The method of claim 1, further comprising arranging the reinforcing structure in an axial direction between the proximal surface and the distal surface of the film.

8. The method of claim 1, further comprising arranging the reinforcing structure in a radial direction between an inner boundary and an outer boundary of the adaptable ostomy base plate.

9. The method of claim 1, further comprising providing the reinforcing structure with more rigidity than the first adhesive layer and more rigidity than the film.

10. The method of claim 1, further comprising providing the reinforcing structure with a greater rigidity along a radial axis than a rigidity of the first adhesive and the film of the adaptable ostomy base plate.

11. The method of claim 1, further comprising providing the user or the healthcare worker with a waste collection bag that is detachable from the adaptable ostomy base plate.

12. The method of claim 1, further comprising providing the user or the healthcare worker with a waste collection bag integrated and attached to the adaptable ostomy base plate.

13. The method of claim 1, further comprising providing the user or the healthcare worker with improved control during application of the adaptable ostomy base plate by:
providing the proximal side of the adaptable ostomy base plate with a curvature configuring an initial engagement of only a portion of the first adhesive with peristomal skin allowing an alignment of the adaptable ostomy base plate around the stoma.

14. The method of claim 1, further comprising providing the user or the healthcare worker with improved control during application of the adaptable ostomy base plate by:
providing the proximal side of the adaptable ostomy base plate with a curvature configuring an initial engagement of only a portion of the first adhesive with peristomal skin allowing visual confirmation of an area located between the peristomal skin and a remaining portion of the first adhesive prior to engaging an entirety of the first adhesive to the peristomal skin.

15. The method of claim 1, further comprising providing the user or the healthcare worker with the adaptable ostomy base plate having a second adhesive on the proximal surface of the film such that the first adhesive and the second adhesive combine to form a proximal side of the adaptable ostomy base plate.

16. The method of claim 1, further comprising providing the user or the healthcare worker with the adaptable ostomy base plate having a second adhesive on the proximal surface of the film, with the second adhesive comprising a hydrocolloid.

17. A method of providing an ostomy device that is shape-adjustable to conform to a bulge or a hernia associated with a stoma, the method comprising:
providing an ostomy base plate comprising: a film forming a distal surface of the ostomy base plate and a first adhesive forming a proximal surface of the ostomy base plate, an undulating outer boundary defined by a plurality of petals, and a reinforcing structure comprising an outer radial periphery attached to the film and an inner radial periphery unattached to the film;
delivering the ostomy base plate in a storage configuration characterized by the proximal surface having a substantially convex shape;
configuring the ostomy base plate to be adaptable to topography of peristomal skin by inverting the storage configuration of the ostomy base plate from the substantially convex shape to a substantially concave shape; and
configuring each of the plurality of petals to fit a different shape of the bulge or the hernia associated with the stoma.

\* \* \* \* \*